United States Patent [19]

Owen et al.

[11] Patent Number: 4,681,437
[45] Date of Patent: Jul. 21, 1987

[54] LASER SCHLIEREN CRYSTAL MONITOR

[75] Inventors: Robert B. Owen; Mary H. Johnston, both of Huntsville, Ala.

[73] Assignee: The United States of America as represented by the Administrator of the National Aeronautics and Space Administration, Washington, D.C.

[21] Appl. No.: 706,565

[22] Filed: Feb. 28, 1985

[51] Int. Cl.[4] .............................................. G01N 21/41
[52] U.S. Cl. ..................................... 356/129; 356/128
[58] Field of Search .................................. 356/129, 128

[56] References Cited

U.S. PATENT DOCUMENTS

| | | | |
|---|---|---|---|
| 2,777,355 | 1/1957 | Lindsey | 356/129 |
| 2,805,599 | 9/1957 | Pajes | 356/129 |
| 4,391,518 | 7/1983 | Owen et al. | 356/129 |
| 4,547,071 | 10/1985 | Teitelbaum | 356/129 |

Primary Examiner—R. A. Rosenberger
Assistant Examiner—Crystal D. Cooper
Attorney, Agent, or Firm—Joseph H. Beumer; John R. Manning; Leon D. Wofford, Jr.

[57] ABSTRACT

A system and method for monitoring the state of a crystal (C) which is suspended in a solution is disclosed which includes providing a light source (10) for emitting a beam (12) of light along an optical axis (X). A collimating lens is arranged along the optical axis for collimating the emitted beam to provide a first collimated light beam (16) consisting of parallel light rays. The solution and crystal are contained in a transparent container (18). By passing the first collimated light beam through the container, a number of the parallel light rays are deflected off of the surfaces of said crystal being monitored according to the refractive index gradient to provide a deflected beam (19) of deflected light rays. A focusing lens (22) is arranged along the optical axis for focusing the deflected rays (32, 34, 48, 50) towards a desired focal point (24a). A knife edge (24) is arranged in a predetermined orientation at the focal point; and a screen (26) is provided. A portion (34, 50) of the deflected beam is blocked with the knife edge to project only a portion (32, 48) of the deflected beam (19). A band (38) is created at one edge of the image of the crystal which indicates the state of change of the surface (39a, 39b) of the crystal (C) being monitored.

10 Claims, 5 Drawing Figures

LASER SCHLIEREN CRYSTAL MONITOR

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

The invention relates to the monitoring of a crystal within a solution to determine whether of not it is growing or dissolving as desired.

Heretofore, the most common noninvasive method used to observe the face of a crystal which is undergoing either growth or dissolution has been to observe the face of the crystal with a measuring microscope. However, this method requires that the microscope monitor be quite close to the crystal and, therefore, only a small portion of the crystal can be examined at a time. The experimenter is usually interested in the crystal as a whole, and this is a considerable disadvantage. The examination of the crystal face in small segmented forms is not a particularly accurate method for determining the state of the crystal as a whole.

Optical systems commonly known as Schlieren systems have been utilized to study density gradients in transparent substances by viewing refractive index gradients. In the Schlieren method, light from a slit is collimated from a lens and focused onto a knife edge by a second lens. The test volume being studied is placed between the two lenses and the deflection pattern that results is viewed on a screen placed behind the knife edge. The deflection is related to the refractive index gradient which is, in turn, related to the density gradient of the test volume. In U.S. Pat. No. 4,391,518 a method is disclosed for utilizing a dual laser optical system for the visualization of phenomena in transparent substances which induce refractive index gradients such as fluid flow and pressure.

While Schlieren techniques are generally well known in the art, their use in monitoring crystal growth has not been heretofore proposed. The prior usages of the well-known Schlieren techniques have not suggested that these techniques would be an expedient to the monitoring of crystal growths.

An important object of the present invention is to provide a technique for monitoring a crystal within a solution to determine whether or not it is growing or dissolving wherein generally the entire face of the crystal may be monitored for accurate testing.

Still another important object of the present invention is to provide a method for monitoring the entire face of a crystal being dissolved or grown in a solution without invading the controlled environment of the solution in which the crystal is being processed.

SUMMARY OF THE INVENTION

The above objectives are accomplished according to the present invention by a novel use of a well-known Schlieren technique. The technique relies upon the refraction of light in order to function. In general, light traveling through a nonuniform medium is refracted in the direction of a positive refractive index gradient. In the case of a growing crystal, material is being absorbed from solution and the density increases as one moves away from a growing face. Light travelling parallel to the face would be refracted away from the surface. In the case of a dissolving crystal, material is being added to solution and the density increases towards a dissolving face. Light travelling parallel to that face would be refracted towards the surface. If the crystal is neither growing nor dissolving, light travelling parallel to the face will be only slightly affected. In accordance with the present invention, light from a laser source is passed through a collimating lens which collimates the light beam and directs the collimated beam through the solution in which the crystal is contained. The parallel rays of the collimated light beam are refracted away from or toward the surface depending on whether the crystal is growing or dissolving, respectively. The collimated beam passing through the solution is then focused onto a knife edge and projected onto a screen where the state of the crystal can be determined by inspecting the image on the screen. Examination of the entire crystal may be had rapidly by simply rotating the knife edge. The entire crystal may be examined at one time. The technique is totally noninvasive and does not require a close proximity to the crystal under study as have the prior methods.

In particular, the technique of the instant invention is advantageous in the monitoring growth crystals in low gravity conditions. The invention has been tested for use in the microgravity of space, and will be used by the crew of Space Lab III in monitoring the growth of crystals in microgravity since it has been found to be the best method for use with the sophisticated experiment in space.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Figure 2:
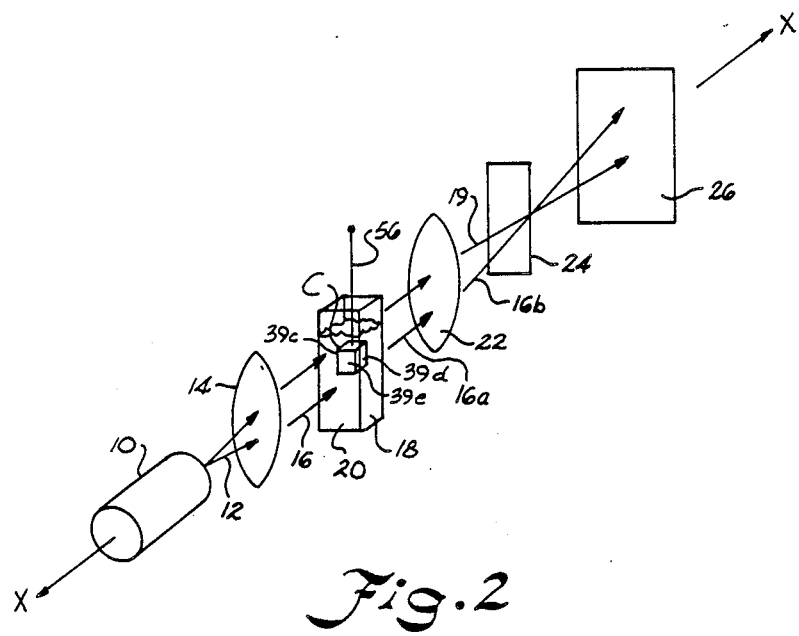
FIG. 2 is a perspective view schematically illustrating an apparatus and method for monitoring a crystal growing or dissolving in a solution in accordance with the present invention.

Referring now in more detail to FIG. 2 of the drawings, an optical system and method for monitoring a crystal growing or dissolving in a solution is disclosed which includes a conventional laser 10 which provides a light source which may be any suitable laser such as a helium neon laser. The light 12 emitted from the laser source 10 passes through a collimating lens 14 which collimates the light beam coming from the laser and provides a first collimated beam 16 of parallel light rays.

A transparent container 18 contains a solution 20 in which the state of a crystal C is being monitored. The collimated light beam 16 passes through the transparent container 18.

Upon passing through the container 18, a number of the rays of the light beam 16 are deflected according to the refractive index gradient of the non-uniform solution surrounding the crystal to form a deflected beam 19. The remaining number of non-deflected rays form a second collimated beam 16a passing through the transparent container. The beams 19 and 16a pass generally through a focusing lens 22 which focuses the rays of the light beams upon a knife edge 24. The knife edge passes the focused rays of the beam 16a in the form of a focused beam 16b upon a screen 26 to provide an image of the crystal for viewing in a well-known and conventional manner.

The knife edge 24 is located at the focal point of lens 22 by adjustment in a conventional manner. A portion of the deflected beam 19 passes by the knife edge onto the screen 26 along with focused beam 16b.

In accordance with the method and technique of the present invention for monitoring a crystal C growing or dissolving as desired in the solution 20, a beam from a light source 10 is collimated by the collimating lens 14 and passed as parallel rays through the container 18 containing the solution 20 and crystal C. If the crystal is growing, material is being absorbed from the solution and the density of the solution increases in a direction away from a growing face of the crystal. The container and crystal are arranged so that light rays 16 travelling parallel to the growing face are refracted away from the face surface due to the increasing density. If the crystal material is being added to the solution in dissolution, the density increases towards the dissolving face of the crystal. According to the method, the light rays 16 travelling parallel to the face are then refracted towards the surface of the crystal. If the crystal is neither growing or dissolving, the light ray 16 travelling parallel to the surface of the crystal will be only slightly effected.

Figure 3:
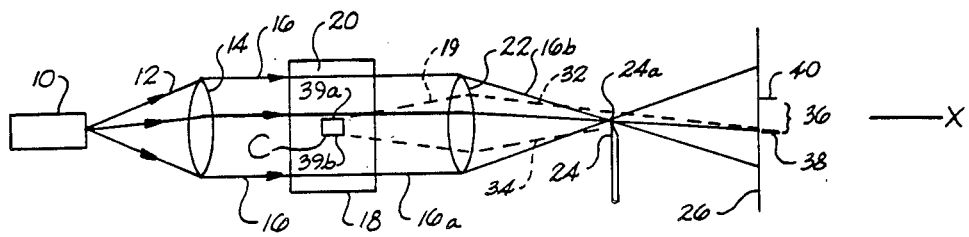
FIG. 3 is a schematic view illustrating an apparatus and method for monitoring a crystal being grown in a solution in accordance with the present invention.

Referring now to FIG. 3, a crystal which is illustrated as being monitored in accordance with the present invention. In this case, the deflected rays are refracted in a direction away from the crystal since light travelling through a nonuniform medium is generally refracted in the direction of a positive refractive index gradient. The deflected rays 32 and 34 are focused onto the knife edge 24 by lens 22. An image 36 of the crystal will appear on the screen and a bright band 38 will appear as the image of the upper face 39a of the crystal. A dark band 40 will appear as the image of the lower face 39b of the crystal, as can best be seen in FIG. 3. The knife edge blocks the lower deflected ray or rays 34 and allows the top deflected rays 32 to pass to form the bright band. The dark band is created by blockage of the deflected rays 34 by the knife edge.

Figure 4:
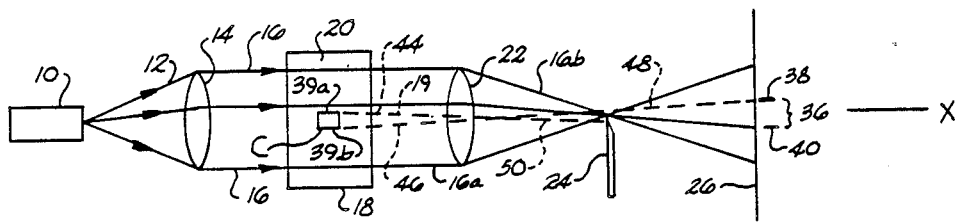
FIG. 4 is a schematic view of apparatus and method for monitoring a crystal being dissolved in a solution according to the present invention.

As can best be seen in FIG. 4, if the crystal is dissolving, the parallel light rays will be refracted towards the dissolving face producing deflected rays 44 and 46. The rays 19 deflected from beam 16 are focused by the focusing lens 22 in the form of rays 48 and 50 towards the knife edge 24. The focused deflected rays 50 are blocked by the knife edge and the focused deflected rays 48 are passed by the knife edge so that the dark band 40 is formed as the image of the upper face of the crystal and a bright band 38 as the lower face image.

Figure 5:
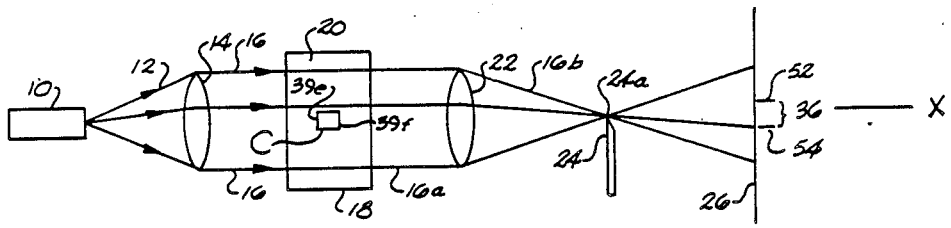
FIG. 5 is a schematic illustration of apparatus and method for monitoring a crystal undergoing transition between growth and dissolution in accordance with the present invention.

If the crystal is neither growing nor dissolving, only minute bands 52 and 54 of light will appear on the screen 26 as can best be seen in FIG. 5.

The entire crystal C can be examined by this method, with perpendicular side faces 39c and 39d of the crystal being examined by rotating the knife edge 24 by 90 degrees about the optical axis X to a vertical position as can best be seen in FIG. 2 wherein the knife edge is parallel to the sides. Examination of forward and rear crystal faces (FIG. 5) 39e and 39f can be had by rotating the crystal itself 90 degrees whereby all six faces are examined by means of a crystal support 56 (FIG. 2).

If it is desired instead to have growth at the upper face indicated by the appearance of a dark band instead of a bright band, an alternate embodiment of the invention would be to simply have the knife edge rotated by 180 degrees around the optical axis X. In this case, the body of the knife edge would be opposite from the way it is shown in the FIGS. 2 through 5.

Thus, it can be seen that a highly advantageous method for monitoring the growth or dissolution of a crystal in a solution can be had according to the present invention. The major advantage of the instant invention over the prior art is that it allows examination of the entire crystal perimeter or circumference rapidly by simply rotating a knife edge. The prior art techniques only consider a small portion of the crystal at a time. Since the experimenter is interested in the crystal as a whole, the instant advantage affords considerable advantages. The technique and method is totally noninvasive and does not require close proximity to the crystal under study as have the prior methods. The method is extremely sensitive and allows examination of particular isolated facets, and permits the growth solution to be examined for convective flows and temperature and concentration gradients. The transition between growth and dissolution can also be studied by the present invention by examining for minute bands.

Figure 1:
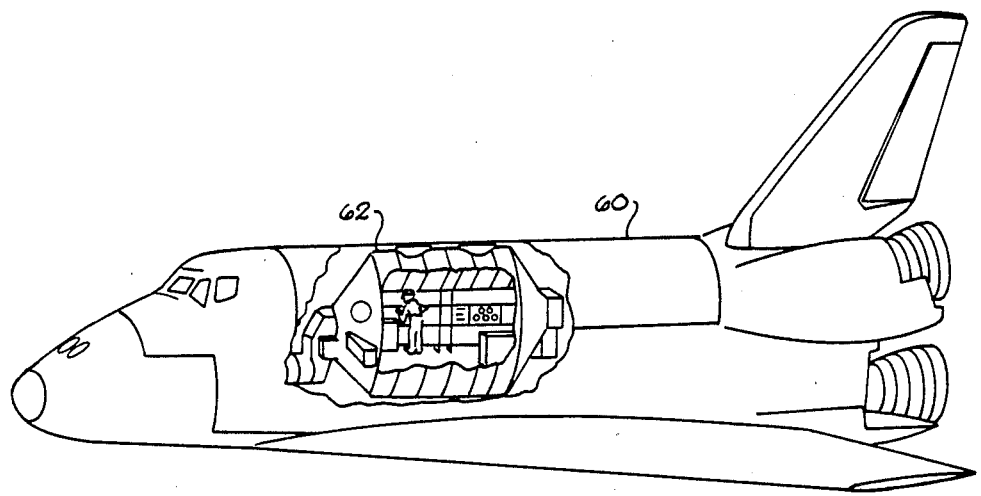
FIG. 1 is a perspective view of a space shuttle vehicle illustrating an application of the invention in monitoring crystal growth or dissolutions in space according to the invention.

The invention is particularly advantageous for monitoring crystal growth in a low-gravity earth orbit such as illustrated in FIG. 1 wherein a space shuttle 60 carries a space lab 62 in which a crystal is grown in space.

In one example of the method of the present invention, the method will be utilized by the crew of Space Lab III to monitor the growth of a triglycine sulphate crystal in microgravity.

While a preferred embodiment of the invention has been described using specific terms, such description is for illustrative purposes only, and it is to be understood that changes and variations may be made without departing from the spirit or scope of the following claims.

What is claimed is:

1. A method for monitoring the state of a crystal to determine whether or not the crystal is growing or dissolving in a solution comprising the steps of:

emitting a light beam from a light source;

collimating said emitted light beam into a first collimated light beam of parallel light rays;

passing said first collimated light beam through said solution in which said crystal is undergoing a change of state so that a first number of the parallel rays in said first collimated beam are deflected in the form of a deflected light beam according to the density gradient of the solution surrounding said crystal;

passing a remaining number of said parallel rays of said collimated beam through said solution in the form of a second collimated beam;

focusing said deflected beam and said second collimated beam at a desired focal point;

disposing a knife edge at said focal point of said focused, deflected beam and said second collimated beam;

passing said second collimated beam past said knife edge to project an image of said crystal upon a screen;

passing a portion of said deflected beam past said knife edge to project a band onto said screen at one end of said crystal image which indicates the growth or dissolution state of said crystal surface being monitored.

2. The method of claim 1 including rotating said knife edge in 90 degree increments to monitor mutually othogonal surfaces of said crystal.

3. The method of claim 1 including arranging said knife parallel to the surface of said crystal being monitored.

4. The method of claim 1 including arranging said knife edge in a horizontal position to monitor a top and bottom surface of said crystal.

5. The method of claim 4 including rotating said knife edge in a vertical orientation to monitor opposing side surfaces of said crystal being monitored.

6. A method of monitoring the state of a crystal which is suspended in a solution comprising the steps of:
providing a light source for emitting a beam of light;
providing a collimating lens having an optical axis for collimating said emitted beam to provide a first collimated light beam consisting of parallel light rays;
providing a transparent container in which said solution and crystal are contained;
passing said first collimated light beam through said container in such a manner that a number of said parallel light rays are deflected by the surfaces of said crystal being monitored providing a deflected beam of said deflected light rays, and a second collimated beam consisting of the remaining parallel light rays of said first collimated beam which are passed through said container;
arranging a focus lens along said optical axis for focusing said deflected rays towards a desired focal point and for focusing the rays of said second collimated beam towards said desired focal point;
arranging a knife edge in a predetermined orientation at said focal point;
providing a screen;
passing said second collimated beam past said knife edge to project an image of said crystal upon said screen;
blocking a portion of said deflected beam with said knife edge to project only a portion of said deflected beam past said knife edge to create a band at one edge of said image of said crystal which indicates the state of change of said surface of said crystal being monitored; and
rotating said knife edge by 90 degrees about the optical axis of the system so that the entire crystal can be examined.

7. The method of claim 6 including arranging said knife edge parallel to the surface of said crystal being monitored.

8. The method claim 6 including projecting a dark band at the outer end of said crystal remote from said optical axis to indicate crystal growth.

9. The method of claim 6 including projecting said deflected beam to create a dark band at the end of said crystal image adjacent the optical axis of said system to indicate a condition of dissolution of said crystal.

10. A system for monitoring the growth or dissolution of a crystal which is suspended in a solution comprising:
an optical system having an optical axis;
a source of light for emitting a concentrated light beam;
a collimating lens located along said optical axis for receiving said concentrated light beam and collimating light rays of said emitted beam into a number of parallel light rays; forming a first collimated beam
a transparent container for containing said solution in which said crystal being monitored is suspended;
said container and crystal being oriented along said optical axis so that said first collimated light beam is passed through said container and a number of said parallel rays of said first collimated beam are deflected from said surface of said crystal being monitored in relation to the density gradient of the nonuniform solution surrounding said crystal to provide a deflected beam and a second collimated beam consisting of nondeflected parallel light rays;
a focusing lens carried along said optical axis on an opposite side of said container for receiving said deflected beam and said second collimated beam and focusing said deflected beam and said collimated beam upon a desired focal point;
a knife edge arranged at said focal point generally parallel to said surfaces of said crystal being monitored;
a screen disposed on a side of said knife edge opposite said focusing lens;
said knife edge being arranged to pass said second collimated beam to project an image of said crystal on said screen; and
said knife edge arranged to block a portion of said deflected beam so that only a portion of said deflected beam is projected on said screen to form a dark band and a bright band at the ends of said image crystal projected on said screen to indicate the state of said surface being monitored.

* * * * *